United States Patent [19]

Falk

[11] 4,208,913
[45] Jun. 24, 1980

[54] HOLDER FOR A STREAM SAMPLER

[76] Inventor: Richard A. Falk, 519 Westminster Dr., Waukesha, Wis. 53186

[21] Appl. No.: 31,568

[22] Filed: Apr. 19, 1979

[51] Int. Cl.² ............................................... G01N 1/12
[52] U.S. Cl. ............................................... 73/425.4 R
[58] Field of Search .................... 73/425.4, DIG. 9

[56] References Cited

U.S. PATENT DOCUMENTS

| | | | |
|---|---|---|---|
| 3,798,974 | 3/1974 | Boron | 73/425.4 R |
| 3,858,857 | 1/1975 | Falk | 73/425.4 R |
| 3,905,238 | 9/1975 | Falk | 73/DIG. 9 |
| 4,069,717 | 1/1978 | Falk | 73/425.4 R |
| 4,166,391 | 9/1979 | McDevitt | 73/425.4 R |

*Primary Examiner*—S. Clement Swisher
*Attorney, Agent, or Firm*—Henry C. Fuller

[57] ABSTRACT

Disclosed herein is a molten metal sampler having disc-shaped metal mold halves which join together to form a neck for a fill tube, and in which a cardboard shield is arranged around the neck. The sampler holder has a notch to wedge at right angles with the fill tube axis and between the mold halves and the shield.

4 Claims, 2 Drawing Figures

HOLDER FOR A STREAM SAMPLER

BACKGROUND OF THE INVENTION

Various techniques have been employed for manipulating molten metal samplers for taking stream samples or immersion or pneumatic samples. Inasmuch as the samplers are used in quantity and the handles or holders may also be discarded after being covered with molten metal at the connection with the sampler, it is desirable that the sampler and handle be relatively inexpensive. Simplification of the parts on the sampler and handle which cooperate to form the connection during their use can save considerable expense for the user of these items.

My U.S. Pat. No. 4,069,717 shows one form of handle for holding a refractory stream sampler. This technique requires recesses in the refractory as well as substantial fabrication of the handle. The use of tapers and sleeves to connect handles with samplers is illustrated in U.S. Pat. Nos. 3,798,974 and 3,905,238. The use of sleeves adds additional expense and can impede retrieval of the sample from the mold parts. My U.S. Pat. No. 3,859,857 discloses a handle for manipulating a stream sampler which employs stamped metal disc-shaped mold halves which make a disc sample. FIGS. 2 and 5 show apparatus that can be employed for this purpose. These handles are costly to manufacture and somewhat difficult to connect to the sampler.

SUMMARY OF THE INVENTION

The invention provides a relatively simple and inexpensive holder and sampler which is easily manufactured and easy to use. The handle or holder is formed from metal tubing with the end flattened. A tapered notch interfits around the neck of the mold halves between the disc-shaped mold parts and a fiber-board disc on the neck.

Further objects, advantages and features of the invention will be apparent from the disclosure.

DESCRIPTION OF THE PREFERRED EMBODIMENT

Figure 1:
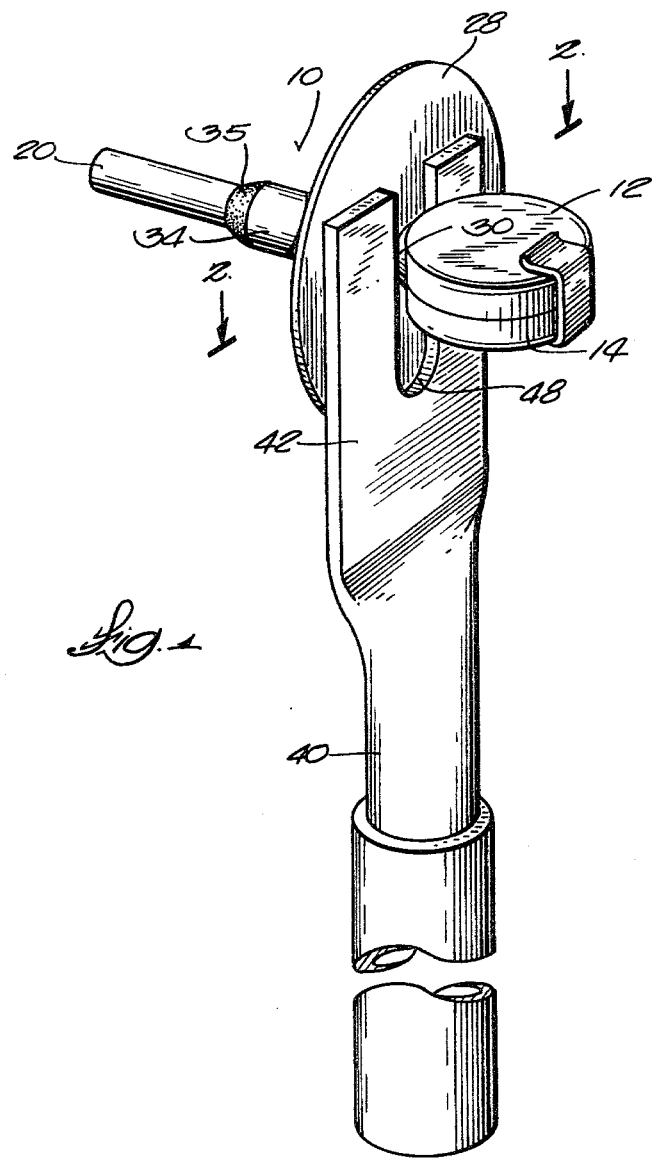
FIG. 1 is a perspective view of the sampler and holder in accordance with the invention.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The molten metal sampler 10 includes two mold halves 12 and 14 which are made of metal and are disc-shaped to provide a disc-shaped sample. Each mold half 12 and 14 includes a projecting portion 16 which together form a cylindrical neck 18 which supports a fused quartz fill tube 20 which communicates with the mold cavity 22. The sampler is provided with a shield 28, which can be fiberboard, to prevent splashing of molten metal around the mold halves. Metal adhering to the mold halves can interfere with retrieval of the sample from the mold. The disc or shield 28 has a central aperture 30 which interfits over the neck 18 of the sampler. The disc is held in place against the annular mold parts by a paperboard sleeve 34 which maintains the disc 28 in tight contact with the mold halves. The sleeve 34 is secured in place by refractory cement at 35.

Figure 2:
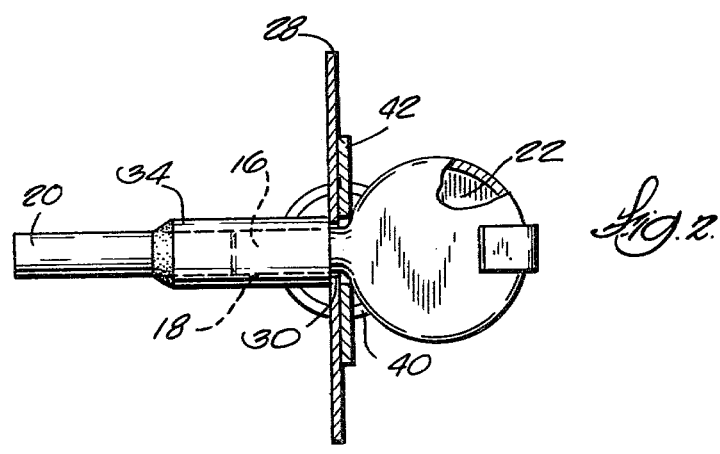
FIG. 2 is a view along line 2—2 of FIG. 1.

The holder of the invention comprises a length of metal tubing 40 which is flattened at one end 42 and notched at 48 with a notch which tapers or converges inwardly. The notch is sized to interfit, as illustrated in FIG. 2, around the neck and provides a wedging fit between the disc 28 and the mold halves.

In use, the handle 40 is at right angles with the fill tube longitudinal axis as shown in FIG. 1.

What is claimed is:

1. In combination, a molten metal sampler and handle for manipulating the sampler for obtaining a sample of molten metal, said sampler comprising a pair of opposed metal mold parts having annular disc-shaped wall portions which cooperate to define a disc-shaped sample, semi-cylindrical projecting portions extending from said disc-shaped sample molds to form a neck for supporting a fill tube, and the improvement comprising a shield arranged around said neck, a sleeve arranged around said neck and pressed against said shield to maintain said shield against said disc-shaped mold parts, and said holder having a bifurcated end with a groove sized to interfit around said neck and wedge between said shield and said disc-shaped mold parts.

2. The combination of claim 1 wherein said handle is formed from pipe and has a flattened portion with the groove being in the flattened portion.

3. The improvement of claim 1 wherein said notch in said handle is tapered inwardly.

4. In combination, a molten metal sampler and handle for manipulating the sampler for obtaining a sample of molten metal, said sampler comprising a pair of opposed metal mold parts having wall portions which cooperate to define a mold cavity, projecting portions extending from said opposed mold parts to form a neck for supporting a fill tube, and the improvement comprising a shield arranged around said neck, a sleeve arranged around said neck and pressed against said shield to maintain said shield against said mold parts, and said holder having a bifurcated end with a groove sized to interfit around said neck and wedge between said shield and said opposed mold parts.

* * * * *